United States Patent
Sredni et al.

(10) Patent No.: US 6,552,089 B1
(45) Date of Patent: *Apr. 22, 2003

(54) METHOD OF TREATING OR PREVENTING ALOPECIA

(76) Inventors: Benjamin Sredni, Shachal 3 Street, Kfar-Saba (IL); Michael Albeck, 8 Harel Street, Ramat-Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 08/758,106

(22) Filed: Nov. 29, 1996

Related U.S. Application Data

(63) Continuation of application No. 08/391,723, filed on Feb. 17, 1995, now abandoned, which is a continuation of application No. 08/109,654, filed on Aug. 20, 1993, now abandoned, which is a continuation of application No. 07/929,681, filed on Aug. 13, 1992, now Pat. No. 5,262,149.

(51) Int. Cl.[7] ................. A61K 31/095; A61K 31/335; A61K 33/00; A01N 25/00

(52) U.S. Cl. ................. 514/706; 514/467; 514/450; 514/457; 514/25; 514/105; 514/880; 424/600

(58) Field of Search .................. 424/10, 600; 514/706, 514/467, 450, 452, 25, 105, 880

(56) References Cited

U.S. PATENT DOCUMENTS 4,761,490 A * 8/1988 Albeck et al. ............. 549/347
5,262,149 A * 11/1993 Sredni et al. .............. 424/10
5,271,925 A * 12/1993 Sredni et al. .............. 424/10

* cited by examiner

*Primary Examiner*—Sreeni Padmanabhan
*Assistant Examiner*—Shengjun Wang
(74) *Attorney, Agent, or Firm*—Hedman & Costigan, P.C.

(57) ABSTRACT

The present application discloses a method of treating alopecia which is based on the use of a tellurium compound such as ammonium trichloro(dioxoethylene-O,O-tellurate).

5 Claims, No Drawings

METHOD OF TREATING OR PREVENTING ALOPECIA

This application is a continuation of Ser. No. 08/391,073, filed Feb. 17, 1995, now abandoned, which was a continuation of Ser. No. 08/109,654, filed Aug. 20, 1993, now abandoned, which was a continuation of Ser. No. 07/929,681, filed Aug. 13, 1992 which is now U.S. Pat. No. 5,262,149.

BACKGROUND OF THE INVENTION

Alopecia which is the partial or complete loss of hair may result from genetic factors, aging, antineoplastic chemotherapy or other causes. Noncicatricial alopecia occurs without scarring or gross atrophic changes. These types of alopecia include males pattern baldness, toxic alopecia, alopecia areata and trichotillomania. In recent years toxic alopecia which is by antineoplastic chemotherapy has become a more common problem as the use of chemotherapy for neoplastic diseases has expanded. This is one of the toxic effects that is seen frequently with alkylating agents, anti-metabolites, plant alkaloids, anti-tumor antibiotics and interferons is alopecia. This problem is particularly distressing to patients who are recovering from chemotherapy because it persists being after any period of hospitalization is required and causes many patients deep psychological difficulties.

Male pattern baldness and other types of alopecia have been resistant to treatment and at the present time, minoxidil is the only recognized therapy for male pattern baldness.

A composition obtained from the bacteria *Serratia marcescens* has been used to protect against the alopecia which is associated with the use of cytosine arabinoside and doxorubicin. This composition had no effect on alopecia which was induced by cyclophosphamide.

The applicants have discovered that noncicatricial or nonscarring alopecia including the alopecia associated with the therapeutic doses of antineoplastic agents may be avoided or reduced by the prior concomitant or subsequent administration of an effective amount of an effective tellurium compound.

It is therefore a primary object of the invention to provide a method for preventing and/or treating alopecia.

It is also an object of the invention to provide a method for preventing alopecia which is induced by antineoplastic agents.

SUMMARY OF THE INVENTION

The invention comprises a method for preventing or treating nonscarring alopecia, said method comprising administering an effective amount of a tellurium compound.

DETAILED DESCRIPTION OF THE INVENTION

The tellurium compounds for use in the invention include those of the formula:

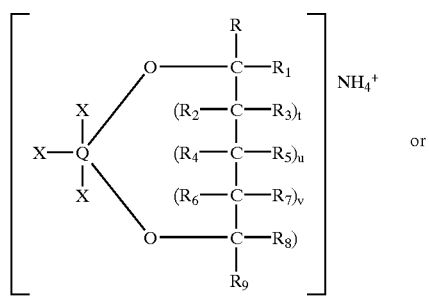

(A)

or

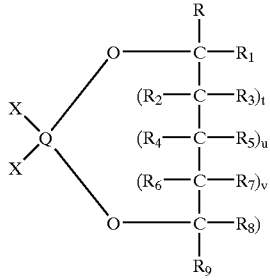

(B)

or

TeO$_2$ or complexes of TeO$_2$     (C)

or

PhTeCl$_3$     (D)

or

TeX$_4$, when X is Cl, Br or F or (C$_6$H$_5$)$_4$P+(TeCl$_3$(O$_2$C$_2$H$_4$))—     (E)

wherein Q is Te or Se; t is 1 or 0; u is 1 or 0; v is 1 or 0; R, R$_1$, R$_2$, R$_3$, R$_4$, R$_5$, R$_6$, R$_7$, R$_8$, and R$_9$ are the same or different and are independently selected from the group consisting of hydrogen, hydroxyalkyl of 1 to 5 carbons, hydroxy, alkyl or from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —COR$_{10}$ wherein R$_{10}$ is alkyl of 1 to 5 carbons; and X is halogen; while the ammonium salt is illustrated, it is understood that other pharmaceutically acceptable salts such as K+ are within the scope of the invention. The compounds with the five membered rings are preferred.

As used herein and in the appended claims, the term alkyl of 1 to 5 carbon atoms includes straight and branched chain alkyl groups such as methyl; ethyl; n-propyl; n-butyl, and the like; the term hydroxyalkyl of 1 to 5 carbon atoms includes hydroxymethyl; hydroxyethyl; hydroxy-n-butyl; the term halkoakyl of 1 to 5 carbon atoms includes chloromethyl; 2-iodoethyl; 4-bromo-n-butyl; iodoethyl; 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —CH$_2$CONH$_2$; —CH$_2$CH$_2$CONH$_2$; —CH$_2$CH$_2$CH$_2$CONH$_2$ and the like; the term cyanoalkyl includes —CH$_2$CN; —CH$_2$CH$_2$CN; —CH$_2$CH$_2$CH$_2$CN and the like; the alkoxy, of 1 to 5 carbon atoms includes methoxy, ethoxy, n-propoxy, n-pentoxy and the like; the terms halo and halogen are used to signify chloro, bromo, iodo and fluoro; the term acyl includes R$_{16}$CO wherein R$_{16}$ is H or alkyl of 1 to 5 carbons such as methanoyl, ethanoyl and the like; the term aryl includes phenyl, alkylphenyl and naphthyl; the term N-monoalkylamidoalkyl includes —$CH_2CH_2CONHCH_3$, —$CH_2CONHCH_2CH_3$; the term N,N-dialkylamidoalkyl includes —$CH_2CON(CH_3)_2$; $CH_2CH_2CON(CH_2$—$CH_3)_2$. Compounds which are based on tellurium are the presently preferred compounds of the invention. The tellurium based compounds that are preferred include those of the formula:

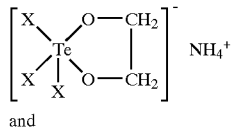
and

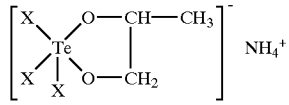

wherein X is halogen. The preferred halogen species is chloro.

Other compounds which are based on tellurium and may be used in the practice of the invention include $PhTeCl_3$, $TeO_2$ and $TeX_4$ $(C_6H_5)_4$ $P+(TeCl_3(O_2C_2H_4))$—(Z. Naturforsh, 36, 307–312 (1981). Compounds of the following structure are also included:

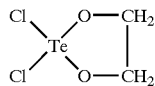

Other compounds useful for the practice of invention include:

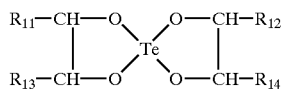

wherein $R_{11}$, $R_{12}$, $R_{13}$ and $R_{14}$ are independently selected from the group consisting of hydrogen, hydroxy-alkyl of 1–5 carbons atoms, hydroxy and alkyl of 1–5 carbons atoms.

Useful dihydroxy compounds for use in the preparation of compounds of structure A or B, include those of formula I wherein R, $R_1$, $R_4$ and $R_5$ are as shown in the Table:

TABLE (I)

$$HO-\underset{\underset{R_1}{|}}{\overset{\overset{R}{|}}{C}}-\underset{\underset{R_5}{|}}{\overset{\overset{R_4}{|}}{C}}-OH$$

| R | $R_1$ | $R_4$ | $R_5$ |
|---|---|---|---|
| H | H | H | H |
| H | Cl | H | H |
| H | $OCH_3$ | H | H |
| H | $COOCH_3$ | H | H |
| H | H | CN | H |
| H | CHO | H | H |
| H | H | COOH | H |
| H | $CH_2COOH$ | H | H |
| H | H | $CH_2COOCH_3$ | H |
| H | I | H | H |
| H | H | Br | H |
| H | H | $CONH_2$ | H |

TABLE-continued (I)

$$HO-\underset{\underset{R_1}{|}}{\overset{\overset{R}{|}}{C}}-\underset{\underset{R_5}{|}}{\overset{\overset{R_4}{|}}{C}}-OH$$

| R | $R_1$ | $R_4$ | $R_5$ |
|---|---|---|---|
| H | H | $CH_2OH$ | H |
| H | COOH | H | H |

Other dihydroxy compounds for use in the preparation of compounds A and B include those of formula II wherein R, $R_1$, $R_2$, $R_3$, $R_4$ and $R_5$ are as shown in the Table:

(II)

$$HO-\underset{\underset{R_1}{|}}{\overset{\overset{R}{|}}{C}}-\underset{\underset{R_3}{|}}{\overset{\overset{R_2}{|}}{C}}-\underset{\underset{R_5}{|}}{\overset{\overset{R_4}{|}}{C}}-OH$$

| R | $R_1$ | $R_2$ | $R_3$ | $R_4$ | $R_5$ |
|---|---|---|---|---|---|
| H | H | H | H | H | H |
| H | H | Cl | H | H | H |
| H | $CH_2OH$ | H | H | H | H |
| H | H | OH | H | H | H |
| H | H | H | $CH_3$ | H | H |
| H | H | H | $CH_2Cl$ | H | H |
| H | H | H | COOH | H | H |
| H | H | H | $CH_2COOH$ | H | H |
| H | H | H | CHO | H | H |
| H | H | H | H | H | $CH_2CHO$ |
| H | H | $CONH_2$ | H | $H_2$ | $CH_3$ |
| H | H | H | CN | H | H |
| H | H | H | H | $CH_2COHN_2$ | H |
| H | H | H | $COOCH_3$ | $H_3$ | H |
| H | $H_3$ | $OCH_3$ | H | H | H |

Other dihydroxy compounds for use in making compound of formula A and B include those of formula III wherein R, $R_1$, $R_2$, $R_3$, $R_4$ and $R_5$ are as shown in the Table.

(III)

$$HO-\underset{\underset{R_1}{|}}{\overset{\overset{R}{|}}{C}}-\underset{\underset{R_3}{|}}{\overset{\overset{R_2}{|}}{C}}-\underset{\underset{R_5}{|}}{\overset{\overset{R_4}{|}}{C}}-\underset{\underset{R_9}{|}}{\overset{\overset{R_8}{|}}{C}}-OH$$

| R | $R_1$ | $R_2$ | $R_3$ | $R_4$ | $R_5$ | $R_8$ | $R_9$ |
|---|---|---|---|---|---|---|---|
| H | H | H | H | H | H | H | H |
| H | H | Cl | H | H | H | H | H |
| H | H | H | H | Br | H | H | H |
| H | H | $OCH_3$ | H | H | H | H | H |
| H | H | $CONH_2$ | H | H | H | H | H |
| H | Br | H | H | H | H | H | H |
| H | H | H | H | $CH_2COOH$ | H | H | H |
| H | H | Cl | Cl | H | H | H | H |
| H | $CH_2COOH$ | H | H | H | H | H | H |
| H | H | $CH_3$ | H | H | H | H | H |
| H | $CH_3$ | H | H | H | H | H | H |
| H | $CH_2Cl$ | H | H | H | H | H | H |
| H | H | H | I | H | H | H | H |
| H | $CH_2CN$ | H | H | H | H | H | H |
| H | H | H | H | $CH_2CH_2OH$ | H | H | H |

Additional dihydroxy compounds include those of formula IV wherein R, $R_1$, $R_2$, $R_3$, $R_4$ and $R_5$ are as shown in the Table.

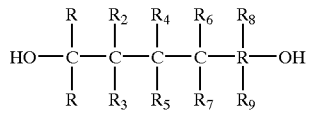

(IV)

| R | R₁ | R₂ | R₃ | R₄ | R₅ | R₆ | R₇ | R₈ | R₉ |
|---|---|---|---|---|---|---|---|---|---|
| H | H | H | H | H | H | H | H | H | H |
| H | H | Cl | H | H | H | Cl | H | H | H |
| H | H | Cl | Cl | H | H | H | H | H | H |
| H | H | CONCH₃ | H | H | H | Br | H | H | H |
| H | H | Br | H | H | H | CON(CH₃)₂ | H | H | H |
| H | H | H | OCH₃ | H | H | H | H | H | H |
| H | H | H | H | OCH₃ | H | H | H | H | H |
| H | H | H | H | CH₂COOH | H | H | H | H | H |
| H | H | COOH | H | H | H | H | H | H | H |
| H | CH₃ | H | H | H | H | H | H | H | H |
| CH₃ | H | H | H | H | H | CH₃ | H | H | H |
| H | CH₂CH₃ | H | H | H | H | H | Cl | H | H |
| H | CH₂CN | H | H | CH₂OH | H | H | H | H | H |
| H | H | H | I | H | H | H | H | CN | H |
| H | CH₂CH₂COOH | H | H | H | H | H | H | H | H |
| H | H | CHO | H | H | H | H | H | H | H |
| H | H | H | F | H | H | H | H | H | H |

Compounds of the following formula are also included:

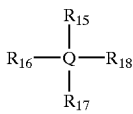

herein R₁₅, R₁₆, R₁₇ and R₁₈ are independently selected from halogen, alkyl of 1–5 carbons; aryl, acyl of 1–5 carbon hydroxyalkyl of 1–5 carbons and aminoalkyl of 1–5 carbons may be made by reacting the appropriate di, tri or tetrahaloselenide or telluride with the appropriate hydroxy compound which may be of the formula: HO—R₁₉; wherein R₁₉; is alkyl of 1 to 5 carbons, haloalkyl of 1 to 5 carbons, aryl, alkylaryl, alkylamido of 1 to 5 carbons, alkylcarbonyl of 1 to 5 carbons, cyanoalkyl of 1 to 5 carbons, cyanoalkyl of 1 to 5 carbons, and an alkoxyalkyl of 2 to 10 carbons. Specific examples of R₁₆ include methyl, ethyl, n-propyl, phenyl, tolyl, amidoethyl, cyanomethyl, methyloxymethyl and CH₂CH₂COOH.

These compounds are described in U.S. Pat. No. 4,761,490 which is incorporated by reference. In addition, TeCl₄; TeBr₄ and compounds which give in aqueous solution TeO₂ prferably in the form of a complex such as for example TeO₂ complex with citric acid or ethylene glycol.

The antineoplastic agents include alkylating agents such as nitrogen mustard, cyclophosphamide, melphan, and chlorambucil. The antimetabolites include purine antagonists such as 6-mercaptopurine and 6-thioguanine; pyrimidine antagonist are cytarabine, 5-fluorouracil, 5-floxuridine, and methotrexate. Plant alkaloids include vincristine, vinblastine, colchicine, etoposide and teniposide. Anti tumor antibiotics include dactinomycin, doxorubicin, daunomycin and mitomycin.

The tellurium compound may be administered by systemic administration by the intramuscular, intravenous or intraperitoneal route to mammals including humans, at doses of 0.025 to 0.5 mg/Kg of body weight every second day.

The invention also includes the treatment or prevention of alopecia by the topical administration of an effective tellurium onto to an area of the body where it is desired to cause hair to grow or to prevent the loss of hair. This aspect of the invention is applicable to the prevention of hair loss and is based on the application of an effective tellurium compound to areas of the body, ie. scalp where hair loss has been noticed. Generally, any non-toxic vehicle may be used as a carrier for the tellurium compound at an effective concentration which will induce hair growth and/or retard and/or prevent hair loss.

Examples of suitable vehicles include petrolatum, Aquaphor, Neobase, propylene glycol, glycerin and the like. These base materials are described in Remington's Pharmaceutical Sciences 17th Ed. Mack Publishing (1985), pp. 1301–1306 which is incorporated herein by reference. Generally, from 1 mg to 2.5 mg/Kg of body weight is applied once daily to the area to be treated. A preferred method of application is based on the use of a vehicle which is a thick liquid having a concentration of 200 µg of tellurium compound/0.2 ml of solution.

When the method of the invention is practiced by parental administration, it may be preferred to administer the tellurium compound by subcutaneous injection at multiple sites (e.g. one injection per sq cm) within the affected area. The doses will be 0.25 mg/Kg to 2.5 mg/Kg of body weight given once daily, or in divided doses in an appropriate vehicle such as PBS. If desired, a dose regimen based on alternate day therapy may be used.

The tellurium compound should be administered prior to the administration of any neoplastic agent for optimal results. Simultaneous or subsequent administration of the tellurium compound with the antineoplastic agent may also be utilized.

The tellurium compound may be administered orally at 2.5 mg/Kg to 7.5 mg/Kg of body weight given once daily. If desired, a dose regimen based on alternate day therapy may be used.

DESCRIPTION OF THE PREFERRED EMBODIMENTS

EXAMPLE 1

The present invention is intended for use primarily in humans. In order to demonstrate the efficacy of the method of the invention, an animal model was chosen to carry out a controlled study to demonstrate the efficacy of the invention according to the method of Hussein et al., Science, Vol. 249, Sept. 28, 1990, pp. 1564–1566.

Sprauge Dawley rats, 8 days old were supplied by the Animal Supply Center of Bar-Ilan University, Israel. Arabinoside (ARC-C) was obtained from the Upjohn Company; cyclophosphamide (CTX) was obtained from Sigma; adriamycin (ADX) was obtained from Farmitalia and ammonium-trichloro (O,O'-dioxoethylene) tellurate was synthesized by the Department of Chemistry, Bar-Ilan University.

Arabinoside was injected intraperitoneally at a dose of 25 or 50 mg/kg day alone or with ammonium-trichloro (O,O'dioxoethylene)tellurate, dissolved in PBS, daily or every other day 2 hours prior to the administration of arabinoside. The cycle of treatment lasted 7 days. On day 9, the results were observed and graded according to the following protocol:

| | |
|---|---|
| No detectable alopecia | 0 |
| Mild alopecia (hair loss <50%) | 1+ |
| Moderately severe alopecia (hair loss >50%) | 2+ |
| Total or virtually total alopecia (hair loss >79%) | 3+ |

The observed results were as follows:

| Treatment | No. of Subjects | Alopecia 0 | 1+ | 2+ | 3+ |
|---|---|---|---|---|---|
| (a) arabinoside-C 25 mg/kg daily (×7 days) | 3 | 0 | 0 | 0 | 3 |
| (b) arabinoside-C 25 mg/kg/i.p. ammonium trichloro (O,O'-dioxoethylene) tellurate 0.5 mg/Kg/IP (daily) (×7 days) | 4 | 0 | 4 | 0 | 0 |
| (c) arabinoside-C 25 mg/kg/i.p. ammonium trichlolo (O,O'-dioxoethylene) tellurate 0.5 mg/Kg/IP (every other day × 7 days) | 4 | 0 | 4 | 0 | 0 |
| (d) arabinoside-C 50 mg/kg/i.p. (×7 days) | 4 | 0 | 0 | 0 | 4 |
| (e) arabinoside-C 50 mg/kg/i.p. ammonium trichloro (O,O'-dioxoethylene) tellurate 0.5 mg/Kg/IP (daily × 7 days) | 4 | 0 | 3 | 1 | 0 |
| (f) arabinoside-C 50 mg/kg/i.p. ammonium trichloro (O,O'-dioxoethylene) tellurate 0.5mg/Kg/IP (every other day × 7 days) | 4 | 0 | 1 | 3 | 0 |

A second experiment was carried out using the same procedure which is outlined above. The results were as follows:

| Treatment | No. of Subjects | Alopecia 0 | 1+ | 2+ | 3+ |
|---|---|---|---|---|---|
| (g) arabinoside-C 25 mg/kg/i.p. (×7 days) | 8 | — | — | — | 8 |
| (h) arabinoside-C 25 mg/kg/i.p. (×7 days) ammonium trichloro (O,O'-dioxoethylene) tellurate 0.5 mg/Kg/IP (daily) (×7 days) | 6 | 6 | — | — | — |
| (i) arabinoside-C 25 mg/kg/i.p. ammonium trichloro (O,O'-dioxoethylene) tellurate 0.5 mg/Kg/IP (every other day ×7 days) | 6 | 6 | — | — | — |
| (j) arabinoside-C 50 mg/kg/i.p. (×7 days) | 8 | — | — | — | 8 |
| (k) arabinoside-C 50 mg/kg/i.p. ×7 days ammonium trichloro (O,O'-dioxoethylene) tellurate 0.5 mg/Kg/IP (daily ×7 days) | 6 | 6 | — | — | — |
| (l) arabinoside-C 50 mg/kg/i.p. ammonium trichloro (O,O'-dioxoethylene) tellurate 0.5 mg/Kg/IP (every other day ×7 days) | 6 | — | 1 | 2 | 3 |

The results of these experiments shows that the addition of ammonium trichloro (O,O'-dioxoethylene)-tellurate to a treatment regimen which is based on arabinoside-C almost completely avoids alopecia when given daily and provides some protection from alopecia when given every other day. A histological examination of the skin of arabinoside-C treated subjects shows almost complete loss of hair follicles while the subjects who are treated with arabinoside-C and ammonium trichloro (O,O'-dioxoethylene) tellurate showed no hair loss or reduced hair loss.

EXAMPLE 2

An experiment was carried out to determine the effect of ammonium trichloro(O,O'-dioxoethylene)tellurate on preventing the alopecia which is induced by cyclophosphamide using the procedure of Example 1.

The results are as follows:

| Treatment | No. of Subjects | Alopecia 0 | 1+ | 2+ | 3+ |
|---|---|---|---|---|---|
| (a) cyclophosphamide 20 mg/kg/i.p. (×7 days) | 8 | — | 2 | 3 | 5 |
| (b) cyclophosphamide 20 mg/kg/i.p. ammonium trichloro (O,O'-dioxoethylene) tellurate 0.5 mg/Kg/IP (daily for 7 days) | 8 | 0 | 4 | 0 | 0 |
| (c) cyclophosphamide 20 mg/kg/i.p. (×7 days) | 10 | — | 3 | 5 | 2 |
| (d) cyclophosphamide 20 mg/kg/i.p. (×7 days) ammonium trichloro (O,O'-dioxoethylene) tellurate 0.5 mg/Kg/IP (daily ×7 days) | 10 | — | 4 | 5 | 1 |

-continued

| Treatment | No. of Subjects | Alopecia 0 | 1+ | 2+ | 3+ |
|---|---|---|---|---|---|
| (e) cyclophosphamide 20 mg/kg/i.p. ×7 days | 5 | 1 | 3 | 1 | — |
| (f) cyclophosphamide 20 mg/kg/i.p. ×7 days ammonium trichloro (0,0'-dioxoethylene) tellurate 0.5 mg/Kg/IP daily ×7 days | 5 | 2 | 2 | 1 | — |
| (g) cyclosphosphamide 20 mg/Kg/i.p. ×7 days | 10 | — | 10 | — | — |
| (h) cyclophosphamide 20 mg/Kg/i.p. ×7 days ammonium trichloro (O,O'-dioxoethylene) tellurate 0.5 mg/Kg/Ip (daily ×7 days) | 10 | 6 | 4 | — | — |

This study shows that ammonium trichloro (O,O'-dioxoethylene)tellurate, at a level of 0.5 mg/kg/i.p., in conjunction with cyclophosphamide provides a mild protection against cyclophosphamide induced alopecia.

EXAMPLE 3

A number of Sprague Dawley rats were subjected to treatment with arabinoside C 25 mg/kg with ammonium trichloro (O,O'-dioxoethylene)tellurate by subcutaneous injection. The control compound was PBS. The results were as follows:

| | Exp. 1 | Exp. 2 | Exp. 3 |
|---|---|---|---|
| ammonium trichloro (O,O'-dioxoethylene) tellurate 0.25 mg/Kg/s.c daily ×7 days | 3/4 | 5/7 | 7/10 |
| PBS | 0/3 | 0/6 | ND* |

*ND = not done

EXAMPLE 4

A stock composition of 1 mg. of ammonium trichloro (O,O'-dioxoethylene) tellurate in 1 ml. of glycerin was prepared. The stock composition was diluted with glycerin to give the following concentrations per ml. so that the stated dose could be applied topically by application of 1 ml. of solution. The solution was applied to the entire back surface of rats once daily for a period of 7 days. Two hours after each treatment the rats were injected with 25 mg/kg of arabinoside-C once daily. Control rats were treated with a glycerin and injected with arabinoside-C. The following results were observed:

| Concentration of Ammonium trichloro (O,O'-dioxoethylene) tellurate (ug/rat) | Grade of Alopecia* | No. of rats in Group |
|---|---|---|
| 200 | 3 | 5 |
| 100 | 2 | 5 |
| 50 | 0 | 5 |
| 20 | 1 | 5 |
| 10 | 3 | 5 |
| 0 | 4 | 5 |

*0 = no alopecia; 1 = less than 20% alopecia; 2 = less than 50% alopecia; 3 = more than 50% alopecia; 4 = total alopecia.

A dose response effect was observed which is attributed to the ammonium trichloro (O,O'-dioxoethylene) tellurate. All control animals that were treated with arabinoside-C showed 100% alopecia whereas 100% of the rats treated with 50 ug of ammonium trichloro (O,O'-dioxoethylene) tellurate showed 0% alopecia.

EXAMPLE 5

A phase II chemotherapy trial was carried out in patients having unresectable and metastatic non-small cell lung tumors. The chemotherapy was based on carboplatinum 300.0 mg/m$^2$/IV daily and etoposide 200.0 mg/m$^2$ on day 3, 5 and 7 for a total of 12 weeks of chemotherapy which was given to group I. In addition to the same chemotherapy, ammonium trichloro (O,O'-dioxoethylene)tellurate was given to Group II at a dose of 3 mg/m$^2$ three times a week starting two weeks before the chemotherapy and continued for 12 weeks after the chemotherapy. The alopecia of both groups was observed 12 weeks after the chemotherapy and was as follows:

| | ALOPECIA SCORE | | | | | |
|---|---|---|---|---|---|---|
| | 0 | I | II | III | IV | Total |
| Group I | 68 45.64% | 22 14.77% | 29 19.46% | 28 18.79% | 2 1.35% | 149 |
| Group II | 122 61.00% | 26 13.00% | 40 20.00% | 12 6.00% | 0 0.00% | 200 |

0 - alopecia
I - casual alopecia
II - >50% alopecia
III - <50% alopecia
IV - total alopecia

We claim:
1. A method for treating male pattern baldness which comprises administering to a patient afflicted with male pattern baldness an effective amount of a tellurium compound of the formula:

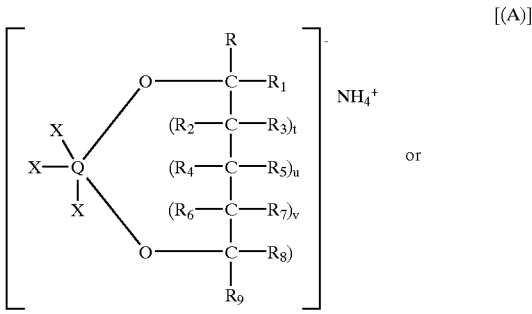

or

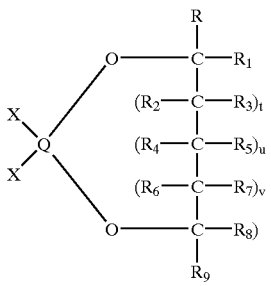

or

TeO$_2$ or

PhTeCl$_3$ or (C$_6$H$_5$)$_4$P+(TeCl$_3$(O$_2$C$_2$H$_4$))—TeX$_4$, wherein Q is Te; t is 1 or 0; u is 1 or 0; v is 1 or 0; R, R$_1$, R$_2$, R$_3$, R$_4$, R$_5$, R$_6$, R$_7$, R$_8$, and R$_9$ are the same or different and are independently selected from the group consisting of hydrogen, hydroxyalkyl of 1 to 5 carbons, hydroxy, alkyl of 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —COR$_{10}$ wherein R$_{10}$ is alkyl of from 1 to 5 carbons; and X is halogen and complexes thereof.

2. A method as defined in claim 1 wherein the tellurium compound is ammonium trichloro (O,O'-dioxoethylene tellurate).

3. A method as defined in claim 1 wherein the tellurium compound is administered parenterally.

4. A method as defined in claim 3 wherein the tellurium compound is administered subcutaneously.

5. A method as defined in claim 1 wherein the tellurium compound is administered topically.

* * * * *

UNITED STATES PATENT AND TRADEMARK OFFICE
CERTIFICATE OF CORRECTION

PATENT NO. : 6,552,089 B1
DATED : April 22, 2003
INVENTOR(S) : Benjamin Sredni

It is certified that error appears in the above-identified patent and that said Letters Patent is hereby corrected as shown below:

<u>Title page,</u>
Item [63], Related U.S. Application Data, replace the first line with the following:
-- Continuation of application No. 08/391,073 filed on Feb... --.

Signed and Sealed this

Second Day of May, 2006

JON W. DUDAS
*Director of the United States Patent and Trademark Office*